(12) United States Patent
Suzuki et al.

(10) Patent No.: US 6,417,410 B1
(45) Date of Patent: Jul. 9, 2002

(54) METHOD FOR PRODUCING ORTHO-ALKYLATED PHENOLS

(75) Inventors: Tomoyuki Suzuki; Fumisato Goto, both of Tsukuba (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/836,216

(22) Filed: Apr. 18, 2001

(30) Foreign Application Priority Data

Apr. 20, 2000 (JP) ........................................ 2000/119398
Jul. 19, 2000 (JP) ........................................ 2000/218858

(51) Int. Cl.$^7$ ............................................. C07C 37/00
(52) U.S. Cl. .................. 568/790; 568/804; 568/628
(58) Field of Search ..................... 568/804, 790, 568/628

(56) References Cited

U.S. PATENT DOCUMENTS

| | | | | |
|---|---|---|---|---|
| 3,959,394 A | * | 5/1976 | Tasaka | |
| 4,329,517 A | * | 5/1982 | Taniguchi | |
| 4,359,591 A | * | 11/1982 | Fremery | |
| 4,400,557 A | * | 8/1983 | Fremery | |
| 4,406,824 A | * | 9/1983 | Fremery | |
| 5,128,304 A | * | 7/1992 | Ito | |

FOREIGN PATENT DOCUMENTS

EP          0419045 A       3/1991
JP          2000-38363 A    2/2000

OTHER PUBLICATIONS

Database WPI, Section Ch, Week 200018, Derwent Publications Ltd., London, GB; Class b05, AN2000–200707, XP002170171, and JP 2000 038363A, (Nippon Shokubai Co, Ltd), Feb. 8, 2000, *abstract*.

* cited by examiner

*Primary Examiner*—Michael L. Shippen
(74) *Attorney, Agent, or Firm*—Birch, Stewart, Kolasch & Birch, LLP

(57) ABSTRACT

A method for producing ortho-alkylated phenols comprising reacting phenols represented by the general formula (1) with monohydric or dihydric alcohol in the presence of germanium oxide under conditions in which said alcohol is in the supercritical condition, wherein each of $R_1$, $R_2$, $R_3$, $R_4$ and $R_5$ independently represents a hydrogen atom, or a linear or branched alkyl group having 1 to 10 carbon atoms.

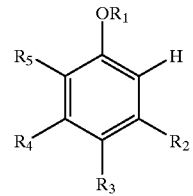

(1)

10 Claims, No Drawings

METHOD FOR PRODUCING ORTHO-ALKYLATED PHENOLS

BACKGROUND OF THE INVENTION

1. Field of the Invention

The present invention relates to a method for producing ortho-alkylated phenols.

2. Description of the Related Art

Aromatic ring alkylated phenols are industrially used as raw materials or intermediates of medical and agricultural chemicals, resins, various additives, polymerization inhibitors, antioxidants, disinfectants, preservatives, industrial chemicals and the like. For example, thymol having a structure in which an isopropyl group is bonded to 2-position and a methyl group is bonded to 5-position of phenol is used as a vermicide.

Conventionally, for producing ortho-alkylated phenols, a gas phase reaction in which phenols and alcohol are vaporized and allowed to flow through a catalyst phase for reaction, a liquid phase reaction utilizing a Friedel and Crafts' reaction, and other methods, are known. JP-A No. 2000-38363 discloses a method in which phenols and alcohol are heated at 400° C. in the supercritical region using zirconium oxide as a catalyst to produce ortho-alkylated phenols. However, this method has a problem that when the reaction is conducted by a batch system, components having higher boiling points composed of dimers of phenols and derivatives thereof as main components are by-produced in large amount.

SUMMARY OF THE INVENTION

An object of the present invention is to provide a method for producing ortho-alkylated phenols from phenols and alcohol, with high selectivity and by-producing a small amount of components having higher boiling points even if the reaction is conducted by a batch system.

The present inventors have intensively studied a method for producing ortho-alkylated phenols by a reaction of phenols with alcohol, and resultantly found that ortho-alkylated phenols can be produced, by reacting phenols with alcohol using germanium oxide as a catalyst under the supercritical condition of the alcohol or by reacting phenols with alcohol in the presence of germanium oxide and carbon dioxide under conditions in which a mixture of alcohol and carbon dioxide is in the supercritical condition, with high selectivity and by-produced a small amount of components having higher boiling points even if the reaction is conducted by a batch system, and have completed the present invention.

Namely, the present invention relates to [I] a method for producing ortho-alkylated phenols comprising reacting phenols represented by the general formula (1) with monohydric or dihydric alcohol in the presence of germanium oxide under conditions in which said alcohol is in the supercritical condition, wherein each of $R_1$, $R_2$, $R_3$, $R_4$ and $R_5$ independently represents a hydrogen atom, or a linear or branched alkyl group having 1 to 10 carbon atoms.

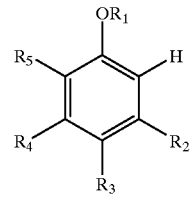

(1)

Further, the present invention relates to [II] the method according to [I], wherein the method comprises reacting phenols represented by the general formula (1) with monohydric or dihydric alcohol in the presence of germanium oxide and carbon dioxide under conditions in which a mixture of said alcohol and carbon dioxide is in the supercritical condition.

DETAILED DESCRIPTION OF THE PREFERRED EMBODIMENTS

The present invention will be illustrated in detail below.

As the linear or branched alkyl group having 1 to 10 carbon atoms represented by $R_1$, $R_2$, $R_3$, $R_4$ and $R_5$ in phenols of the general formula (1) used as a starting raw material in the present invention, amethyl group, ethyl group, n-propyl group, isopropyl group, n-butyl group, isobutyl group, t-butyl group and the like are listed, and as specific examples of phenols of the general formula (1), phenol, o-cresol, m-cresol, p-cresol, 2,3-xylenol, 2,4-xylenol, 2,5-xylenol, 3,4-xylenol, 3,5-xylenol, anisole, t-butylphenol and the like are listed.

In the present invention, the alcohol which is another starting raw material is not particularly restricted providing it is monohydric or dihydric alcohol, and it is preferably monohydric alcohol of the general formula (2):

$R_6$—OH (2)

(wherein, $R_6$ represents a linear or branched alkyl group having 1 to 10 carbon atoms). Here, a methyl group, ethyl group, n-propyl group, isopropyl group, n-butyl group, isobutyl group, t-butyl group and the like are listed as $R_6$.

As themonohydric alcohol of the general formula (2), methanol, ethanol, n-propanol, isopropanol, n-butanol, isobutanol, t-butanol, pentanol, hexanol, heptanol, n-octanol, n-nonanol, n-decanol and the like are specifically listed, and because of high selectivity, methanol, ethanol, n-propanol and n-butanol are preferable, methanol and ethanol are more preferable, methanol is further preferable.

As the dihydric alcohol, ethylene glycol, propylene glycol and the like are listed.

In the present invention, the molar ratio of monohydric or dihydric alcohol to phenols of the general formula (1) is appropriately determined depending on compounds used, and generally from 1 to 1000, and ratios from 1 to 200 are preferably used.

Substances have inherent three conditions, gas, liquid and solid, and further, at the critical temperature or more and critical pressure or more, a fluid phase exists which is not condensed even if it is pressed. This condition is called the supercritical condition.

When a substance is chemically reacted in fluid under the supercritical condition, this substance may manifest higher reactivity than in fluid under gas phase condition and in fluid under liquid phase condition, the reason for this being not apparent, and being guessed that the fluid under the supercritical condition presumably has high density and high diffusion property.

Further, under the supercritical condition, the size of a reaction apparatus can be decreased as compared with the gas phase reaction since the supercritical condition has a density near liquid phase.

In the present invention, the upper limit of the reaction temperature is not restricted, and preferably 450° C. or less so that phenols of the general formula (1) are not decomposed. The upper limit of the reaction pressure also is not restrictive, and preferably 25 MPa or less since it is expensive to increase pressure resistance of a reaction apparatus.

In the production method [I] of the present invention, a reaction is conducted under conditions in which monohydric or dihydric alcohol is in the supercritical condition in the presence of germanium oxide. When methanol is used as this alcohol, the reaction is conducted under conditions of 240° C. or more and 8MPa or more since methanol has a critical temperature of 240° C. and a critical pressure of 8 MPa. When ethanol is used, the reaction is conducted under conditions of 243° C. or more and 6.3 MPa or more since ethanol has a critical temperature of 243° C. and a critical pressure of 6.3 MPa. When n-propanol is used, the reaction is conducted under conditions of 264° C. or more and 5 MPa or more since n-propanol has a critical temperature of 264° C. and a critical pressure of 5 MPa. When isopropanol is used, the reaction is conducted under conditions of 235° C. or more and 4.8 MPa or more since isopropanol has a critical temperature of 235° C. and a critical pressure of 4.8 MPa. When n-butanol is used, the reaction is conducted under conditions of 287° C. or more and 4.8 MPa or more since n-butanol has a critical temperature of 287° C. and a critical pressure of 4.8 MPa.

Next, the production method [II] of the present invention will be illustrated.

In the production method [II] of the present invention, a reaction is conducted in the presence of germanium oxide and carbon dioxide under conditions in which a mixture of monohydric or dihydric alcohol and carbon dioxide is in the supercritical condition.

The mixing ratio of the above-mentioned alcohol to carbon dioxide is not particularly restricted, and determined in view of the solubility of phenols of the general formula (1) used in the reaction into the above-mentioned alcohol. The mixing ratio of the above-mentioned alcohol to carbon dioxide is preferably from 10:90 to 99:1.

A case in which methanol is used as the above-mentioned alcohol and phenol is used as the phenols of the general formula (1) will be specifically illustrated. For example, in the case of a mixture having a molar ratio of methanol to carbon dioxide of 75:25, this mixture has a critical temperature of 204° C. and a critical pressure of 12.75 MPa according to J. Chem. Thermodynamics, vol. 23, p. 970 (1991).

When ortho-methylation of phenols is conducted under temperature and pressure conditions in which a mixture of methanol and carbon dioxide is in the supercritical condition, temperature and pressure conditions are necessary under which the mixture is in the supercritical condition. For example, in the case of the above-mentioned mixture having a molar ratio of methanol to carbon dioxide of 75:25, it is necessary to conduct the reaction at a temperature of 204° C. or more and a pressure of 12.75 MPa or more, and the reaction is preferably conducted at a temperature of 240° C. or more and a pressure of 12.75 MPa or more.

The reaction times in the production method [I] of the present invention and the production method [II] of the present invention are appropriately determined depending on the kinds of the phenols and the alcohol, respectively, and the like, and usually in the range from 1 minute to 24 hours.

In the respective production methods of the present invention, it is preferable to effect a batch system reaction of phenols with monohydric or dihydric alcohol using as germanium oxide as a catalyst, and by adopting such a reaction embodiment, by-production of components having higher boiling points composed of dimers of phenols and derivatives thereof as main components is suppressed, and selectivity of ortho-alkylated phenols increases.

Further, the amount of germanium oxide added as a catalyst maybe small, and the amount of germanium oxide added is preferably from 0.05 to 50% by weight, more preferably from 0.1 to 30% by weight, further preferably from 0.5 to 10% by weight based on phenols of the general formula (1).

In any of the production method [I] and the production method [II] of the present invention, it may be conducted by a batch system or by a flow system, and the batch system is preferable.

In any of the production method [I] and the production method [II] of the present invention, since the reaction mixture after completion of the reaction may sometimes contain unreacted raw materials or by-products or impurities in addition to ortho-alkylated phenols of the general formula (1), the ortho-alkylated phenols of the general formula (1) can be separated and purified to purities required for various uses. The separation and purification methods are not particularly restricted, and methods industrially usually used such as distillation, extraction and the like can be applied.

According to the production method of the present invention, ortho-alkylated phenols can be produced from phenols of the general formula (1) and monohydric or dihydric alcohol, using a relatively small reaction vessel, at high selectivity under conditions in which by-production of components having higher boiling points such as dimers of phenols and derivatives thereof and the like is small. The production methods of the present invention have also characteristics that a reaction is possible even if the amount of a catalyst is small, and that by-production of components having higher boiling points is small particularly in the batch system.

According to the method of the present invention, ortho-alkylated phenols can be produced from phenols and alcohol using a relatively small reaction vessel with high selectivity under conditions in which by-production of components having higher boiling points such as dimers of phenols and derivatives thereof, even if the reaction is conducted by batch system, therefore, the method of the present invention is industrially useful.

EXAMPLES

The following examples illustrate the present invention further in detail, but do not limit the scope of the present invention.

Reaction materials and products in examples were identified by using a gas chromatography mass selective detector, HP-6890 (GC: manufactured by Yokogawa Electric Corp.)-HP5973 (MS: manufactured by Yokogawa Electric Corp.), and quantitatively analyzed using a gas chromatography apparatus, GC-353B (manufactured by GL Science) equipped with FID (flow ionization detector). Conversions and selectivities in examples were calculated by the following methods. The conversion was calculated using the formula: (conversion) (%)={1−(area of chromatograph of reaction substrate remaining unreacted in reaction liquid)/

(sum of areas of chromatograph of remaining reaction substrate and all reaction products)}×100. Further, selectivity was calculated, hypothesizing areas of gas chromatograph per mol of reaction products are the same, using the formula: (selectivity) (%)={(area of gas chromatograph of reaction product to be calculated)/(sum of areas of gas chromatograph of all reaction products)}×100.

Example 1

0.460 g of phenol (manufactured by Wako Pure Chemical Industries Ltd.), 1.451 g of methanol (manufactured by Wako Pure Chemical Industries Ltd.) and 0.030 g of germanium oxide ($GeO_2$, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature (ca. 25° C.), then, the reaction liquid was removed out of the autoclave. Namely, the reaction was conducted by batch system. Quantification was conducted by the above-mentioned method to find that the conversion of phenol was 44 mol %, the selectivity of o-cresol was 71 mol %, the selectivity of 2,6-xylenol was 25 mol %, the selectivity of anisole was 1 mol %, and the production amount of components having higher boiling points composed of dimers of phenol of the following chemical formula (5) and derivative thereof as main components was as small as 3 mol % intotal. p-cresol, 2,4-xylenol and2,4,6-trimethylphenol were not produced. Components were separated from the reaction liquid by using liquid chromatography (elution liquid; water and methanol), and o-cresol and 2,6-xylenol were separated out from them. The separated liquid was analyzed by using a gas chromatography mass selective detector, to confirm that o-cresol and 2,6-xylenol were separated from the products. Since this autoclave was not equipped with a pressure gauge, the following experiment was conducted to estimate the pressure during the reaction. Namely, a pressure gauge was installed to the same autoclave, phenol and methanol in the same amounts were charged, and the mixture was heated up to 400° C. in a sand bath, and the pressure was measured. The estimated pressure during the reaction was 15.4 MPa.

A higher boiling point component of the formula:

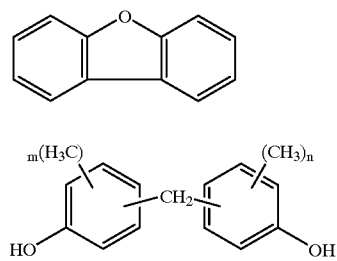

(5)

wherein, each of m and n independently represents an integer from 0 to 4.

Comparative Example 1

0.403g of phenol, 1.405 g of methanol and 0.031 g of zirconium oxide ($ZrO_2$, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 3 mol %, the selectivity of o-cresol was 49 mol %, the selectivity of p-cresol was 2 mol %, the selectivity of anisole was 13 mol %, and the production amount of components having higher boiling points composed of dimers of phenol of the above-described chemical formula (5) and derivative thereof as main components was 32 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 15.0 MPa.

Comparative Example 2

0.411 g of phenol, 1.363 g of methanol and 0.031 g of titanium oxide ($TiO_2$, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 24 mol %, the selectivity of o-cresol was 43 mol %, the selectivity of 2,6-xylenol was 2 mol %, the selectivity of p-cresol was 2 mol %, the selectivity of 2,4-xylenol was 1 mol %, the selectivity of anisole was 9 mol %, and the production amount of components having higher boiling points composed of dimers of phenol of the above-described chemical formula (5) and derivative thereof as main components was 42 mol % in total. 2,4,6-trimethylphenol was not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 3

0.407 g of phenol, 1.353 g of methanol and 0.031 g of niobium oxide ($Nb_2O_5$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 8 mol %, the selectivity of o-cresol was 16 mol %, the selectivity of p-cresol was 2 mol %, the selectivity of anisole was 22 mol %, and the production amount of components having higher boiling points composed of dimers of phenol of the above-described chemical formula (5) and derivative thereof as main components was 53 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 4

0.408 g of phenol, 1.353 g of methanol and 0.032 g of chromium oxide ($Cr_2O_3$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 5 mol %, the selectivity of o-cresol was 16 mol %, the selectivity of p-cresol was 1 mol %, the selectivity of anisole was 6 mol %, and the production amount of components having higher boiling points composed of dimers of phenol of the above-described chemical formula (5) and derivative thereof as main components was 71 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during there action was 14.7 MPa.

Comparative Example 5

0.410g of phenol, 1.355 g of methanol and 0.031 g of molybdenum oxide ($MoO_3$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 97 mol %, the selectivity of o-cresol was 22 mol %, the selectivity of 2,6-xylenol was 39 mol %, the selectivity of 2,4-xylenol was 3 mol %, the selectivity of anisole was 2 mol %, the selectivity of 2,4,6-trimethylphenol was 9 mol % and the production amount of components having higher boiling points composed of dimers of phenol of the above-described chemical formula (5) and derivative thereof as main components was 19 mol % in total. p-cresol was not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 6

0.410g of phenol, 1.363 g of methanol and 0.031 g of tungsten oxide ($WO_3$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 21 mol %, the selectivity of o-cresol was 16 mol %, the selectivity of 2,6-xylenol was 1 mol %, the selectivity of p-cresol was 4 mol %, the selectivity of 2,4-xylenol was 1 mol %, the selectivity of anisole was 21 mol % and the production amount of component shaving higher boiling points composed of dimers of phenol of the above-described chemical formula (5) and derivative thereof as main components was 51 mol % in total. 2,4,6-trimethylphenol was not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 7

0.405 g of phenol, 1.358 g of methanol and 0.031 g of manganese oxide ($MnO_2$, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 19 mol %, the selectivity of o-cresol was 39 mol %, the selectivity of 2,6-xylenol was 1 mol %, the selectivity of p-cresol was 1 mol %, the selectivity of 2,4-xylenol was 1 mol %, the selectivity of anisole was 2 mol % and the production amount of components having higher boiling points composed of dimers of phenol of the above-described chemical formula (5) and derivative thereof as main components was 54 mol % in total. 2,4,6-trimethylphenol was not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 8

0.401 g of phenol, 1.354 g of methanol and 0.031 g of iron oxide ($Fe_2O_3$, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 21 mol %, the selectivity of o-cresol was 70 mol %, the selectivity of 2,6-xylenol was 4 mol %, the selectivity of anisole was 1 mol % and the production amount of components having higher boiling points composed of dimers of phenol of the above-described chemical formula (5) and derivative thereof as main components was 24 mol % in total. p-cresol, 2,4-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 9

0.413 g of phenol, 1.364 g of methanol and 0.032 g of cobalt oxide (CoO, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 48 mol %, the selectivity of o-cresol was 31 mol %, the selectivity of 2,6-xylenol was 2 mol %, the selectivity of p-cresol was 1 mol % and the production amount of components having higher boiling points composed of dimers of phenol of the above-described chemical formula (5) and derivative thereof as main components was 6 mol % in total. 2,4-xylenol, anisole and 2,4,6-trimethylphenol were not produced. In this reaction, hydrogenation of an aromatic ring progressed, and consequently, cyclohexanol was produced in a selectivity of 15 mol % and cyclohexanone was produced in a selectivity of 38 mol %. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 10

0.415 g of phenol, 1.359 g of methanol and 0.031 g of zinc oxide (Zno, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 5 mol %, the selectivity of o-cresol was 27 mol %, the selectivity of p-cresol was 2 mol %, the selectivity of anisole was 5 mol % and the production amount of components having higher boiling points composed of dimers of phenol of the above-described chemical formula (5) and derivative thereof as main components was 63 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 11

0.414 g of phenol, 1.360 g of methanol and 0.031 g of aluminum oxide ($Al_2O_3$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 19 mol %, the selectivity of o-cresol was 17 mol %, the selectivity of p-cresol was 1 mol %, the selectivity of anisole was 51 mol % and the production amount of components having higher boiling points composed of dimers of phenol of the above-described chemical formula (5) and derivative thereof as main components was 28 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 12

0.415 g of phenol, 1.356 g of methanol and 0.031 g of indium oxide ($In_2O_3$, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 23 mol %, the selectivity of o-cresol was 52 mol %, the selectivity of 2,6-xylenol was 2 mol %, the selectivity of p-cresol was 1 mol %, the selectivity of anisole was 3 mol % and the production amount of components having higher boiling points composed of dimers of phenol of the above-described chemical formula (5) and derivative thereof as main components was 40 mol % in total. 2,4-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 13

0.402 g of phenol (manufactured by Wako Pure Chemical Industries Ltd.), 1.353 g of methanol (manufactured by Wako Pure Chemical Industries Ltd.) and 0.031 g of silicon oxide ($SiO_2$, manufactured by Nitto Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 17 mol %, the selectivity of o-cresol was 14 mol %, the selectivity of p-cresol was 1 mol %, the selectivity of anisole was 2 mol % and the production amount of components having higher boiling points composed of dimers of phenol of the above-described chemical formula (5) and derivative thereof as main components was 81 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 14

0.389 g of phenol, 1.372 g of methanol and 0.029 g of tin oxide ($SnO_2$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 24 mol %, the selectivity of o-cresol was 25 mol %, the selectivity of 2,6-xylenol was 1 mol %, the selectivity of p-cresol was 1 mol %, the selectivity of anisole was 1 mol % and the production amount of components having higher boiling points composed of dimers of phenol of the above-described chemical formula (5) and derivative thereof as main components was 71 mol % in total. 2,4-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 15

0.408 g of phenol, 1.354 g of methanol and 0.031 g of magnesium oxide (MgO, manufactured by Kojundo Kagaku K.K.) were charged in an autoclave (made of SUS316, inner volume 4.5 ml, no pressure gauge), the mixture was heated up to 400 ° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 3 mol %, the selectivity of o-cresol was 23 mol %, the selectivity of p-cresol was 2 mol %, the selectivity of anisole was 29 mol % and the production amount of components having higher boiling points composed of dimers of phenol of the above-described chemical formula (5) and derivative thereof as main components was 36 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 16

0.407 g of phenol, 1.357 g of methanol and 0.031 g of calcium oxide (CaO, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 10 mol %, the selectivity of o-cresol was 45 mol %, the selectivity of 2,6-xylenol was 1 mol %, the selectivity of p-cresol was 11 mol %, the selectivity of 2,4-xylenol was 1 mol %, the selectivity of anisole was 8 mol % and the production amount of components having higher boiling points composed of dimers of phenol of the above-described chemical formula (5) and derivative thereof as main components was 32 mol % in total. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 17

0.406 g of phenol, 1.353 g of methanol and 0.031 g of strontium oxide (SrO, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 61 mol %, the selectivity of o-cresol was 43 mol %, the selectivity of 2,6-xylenol was 6 mol %, the selectivity of p-cresol was 13 mol %, the selectivity of 2,4-xylenol was 8 mol %, the selectivity of anisole was 13 mol %, the selectivity of 2,4,6-trimethylphenol was 1 mol %, and the production amount of components having higher boiling points composed of dimers of phenol of the above-described chemical formula (5) and derivative thereof as main components was 13 mol % in total. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 18

0.411 g of phenol, 1.361 g of methanol and 0.030 g of barium oxide (BaO, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 38 mol %, the selectivity of o-cresol was 24 mol %, the selectivity of 2,6-xylenol was 1 mol %, the selectivity of p-cresol was 16 mol %, the selectivity of 2,4-xylenol was 3 mol %, the selectivity of anisole was 8 mol % and the production amount of components having higher boiling points composed of dimers of phenol of the above-described chemical formula (5) and derivative thereof as main components was 46 mol % in total. 2,4,6-trimethylphenol was not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 19

0.401 g of phenol, 1.355 g of methanol and 0.030 g of yttrium oxide ($Y_2O_5$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 2 mol %, the selectivity of o-cresol was 17 mol %, the selectivity of p-cresol was 1 mol %, the selectivity of anisole was 10 mol % and the production amount of components having higher boiling points composed of dimers of phenol of the above-described chemical formula (5) and derivative thereof as main components was 66 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 20

0.419 g of phenol, 1.357 g of methanol and 0.030 g of lanthanum oxide ($La_2O_3$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 4 mol %, the selectivity of o-cresol was 26 mol %, the selectivity of p-cresol was 2 mol %, the selectivity of anisole was 9 mol % and the production amount of components having higher boiling points composed of dimers of phenol of the above-described chemical formula (5) and derivative thereof as main components was 59 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 21

0.401 g of phenol, 1.357 g of methanol and 0.030 g of nickel oxide (NiO, manufactured by Hanni Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 9 mol %, the selectivity of o-cresol was 27 mol %, the selectivity of p-cresol was 1 mol %, the selectivity of anisole was 4 mol % and the production amount of components having higher boiling points composed of dimers of phenol of the above-described chemical formula (5) and derivative thereof as main components was 63 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 22

0.400 g of phenol, 1.352 g of methanol and 0.031 g of samarium oxide ($Sm_2O_3$, manufactured by Kojundo Kagaku K.K.) were charged in an autoclave (made of SUS316, inner volume 4.5 ml, no pressure temperature, then, the reaction liquid was removed out of the autoclave. Quantification was conducted by the above-mentioned method to find that the conversion of phenol was 5 mol %, the selectivity of o-cresol was 20 mol %, the selectivity of p-cresol was 1 mol %, the selectivity of anisole was 20 mol % and the production amount of components having higher boiling points composed of dimers of phenol of the above-described chemical formula (5) and derivative thereof as main components was 53 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 24

0.406 g of phenol, 1.441 g of methanol and 0.030 g of copper oxide (CuO, manufactured by Kojundo Kagaku K.K.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to gauge), the mixture was heated up to 400° C. in a sand bath to initiate the reaction. 30 minutes after, the autoclave was quenched, and the temperature was returned to room temperature, then, the reaction liquid was removed out of the autoclave. Quantification was conducted by the above-mentioned method to find that the conversion of phenol was 6 mol %, the selectivity of o-cresol was 17 mol %, the selectivity of p-cresol was 2 mol %, the selectivity of anisole was 5 mol % and the production amount of components having higher boiling points composed of dimers of phenol of the above-described chemical formula (5) and derivative thereof as main components was 73 mol % in total. 2,4-xylenol, 2,6-xylenol and 2,4,6-trimethylphenol were not produced. Pressure was measured in the same manner as in Example 1 except that phenol and methanol were charged in the same amounts as described above into the same autoclave, and the pressure during the reaction was estimated. The estimated pressure during the reaction was 14.7 MPa.

Comparative Example 23

0.404 g of phenol, 1.359 g of methanol and 0.031 g of tantalum oxide($Ta_2O_3$, manufactured by Wako Pure Chemical Industries Ltd.) were charged in an autoclave (made of SUS316, inner volume 4.5 ml, no pressure gauge), the mixture was heated up to 400° C. in a sand bath to initiate the reaction. 30 minutes after, the autoclave was quenched, and the temperature was returned to room find that the conversion of phenol was 43 mol %, the selectivity of o-cresol was 32 mol %, the selectivity of 2,6-xylenol was 3 mol %, the selectivity of p-cresol was 2 mol %, the selectivity of 2,4-xylenol was 1 mol %, the selectivity of anisole was 1 mol % and the production amount of components having higher boiling points composed of dimers of phenol of the above-described chemical formula (5) and derivative thereof as main components was 53 mol % in total. 2,4,6-trimethylphenol was not produced. Pressure was measured in the same manner as in Example 1 except that phenol and methanol were charged in the same amounts as described above into the same autoclave, and the pressure during the reaction was estimated. The estimated pressure during the reaction was 15.3 MPa.

The results of Example 1 and Comparative Examples 1 to 24 are summarized in the following Table 1.

TABLE 1

| No. | Conversion (% by mole) | Selectivity (% by mole) | | | |
|---|---|---|---|---|---|
| | | OCL | 26Xyl | OMP | HBP |
| Ex. 1 | 44 | 71 | 25 | 96 | 3 |
| Com. 1 | 3 | 49 | 0 | 49 | 32 |

TABLE 1-continued

| No. | Conversion (% by mole) | Selectivity (% by mole) | | | |
|---|---|---|---|---|---|
| | | OCL | 26Xyl | OMP | HBP |
| Com. 2 | 24 | 43 | 2 | 45 | 42 |
| Com. 3 | 8 | 16 | 0 | 16 | 53 |
| Com. 4 | 5 | 16 | 0 | 16 | 71 |
| Com. 5 | 97 | 22 | 39 | 61 | 19 |
| Com. 6 | 21 | 16 | 1 | 17 | 51 |
| Com. 7 | 19 | 39 | 1 | 40 | 54 |
| Com. 8 | 21 | 70 | 4 | 74 | 24 |
| Com. 9 | 48 | 31 | 2 | 33 | 6 |
| Com. 10 | 5 | 27 | 0 | 27 | 63 |
| Com. 11 | 19 | 17 | 0 | 17 | 28 |
| Com. 12 | 23 | 52 | 2 | 54 | 40 |
| Com. 13 | 17 | 14 | 0 | 14 | 81 |
| Com. 14 | 24 | 25 | 1 | 26 | 71 |
| Com. 15 | 3 | 23 | 0 | 23 | 36 |
| Com. 16 | 10 | 45 | 1 | 46 | 32 |
| Com. 17 | 61 | 43 | 6 | 49 | 13 |
| Com. 18 | 38 | 24 | 1 | 25 | 46 |
| Com. 19 | 2 | 17 | 0 | 17 | 66 |
| Com. 20 | 4 | 26 | 0 | 26 | 59 |
| Com. 21 | 9 | 27 | 0 | 27 | 63 |
| Com. 22 | 6 | 17 | 0 | 17 | 73 |
| Com. 23 | 5 | 20 | 0 | 20 | 53 |
| Com. 24 | 43 | 32 | 3 | 35 | 53 |

OCL: o-cresol; 26Xyl: 2,6-Xylenol
OMP: total of all ortho-methylated phenols
HBP: components having higher boiling points composed of dimers of phenol of the above-described chemical formula (5) and derivative

What is claimed is:

1. A method for producing ortho-alkylated phenols comprising reacting phenols represented by the general formula (1) with monohydric or dihydric alcohol in the presence of germanium oxide under conditions in which said alcohol is in the supercritical condition, wherein each of $R_1$, $R_2$, $R_3$, $R_4$ and $R_5$ independently represents a hydrogen atom, or a linear or branched alkyl group having 1 to 10 carbon atoms.

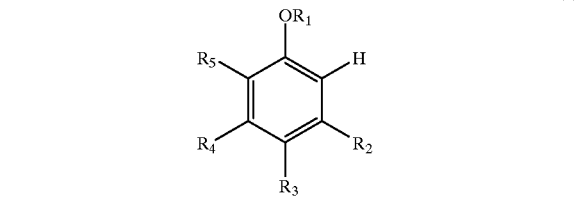
(1)

2. The method according to claim 1, wherein the method comprises reacting phenols represented by the general formula (1) with monohydric or dihydric alcohol in the presence of germanium oxide and carbon dioxide under conditions in which a mixture of said alcohol and carbon dioxide is in the supercritical condition.

3. The method according to claim 1, wherein the alcohol is monohydric alcohol.

4. The method according to claim 2, wherein the alcohol is monohydric alcohol.

5. The method according to claim 3, wherein the monohydric alcohol is alcohol represented by the general formula (2), wherein, $R_6$ represents a linear or branched alkyl group having 1 to 10 carbon atoms.

$$R_6\text{—OH} \quad (2)$$

6. The method according to claim 4, wherein the monohydric alcohol is alcohol represented by the general formula (2), wherein, $R_6$ represents a linear or branched alkyl group having 1 to 10 carbon atoms.

$$R_6\text{—OH} \quad (2)$$

7. The method according to claim 5, wherein $R_6$ in the general formula (2) is a methyl group.

8. The method according to claim 6, wherein $R_6$ in the general formula (2) is a methyl group.

9. The method according to claim 1, wherein germanium oxide is added in the amount of from 0.1 to 30% by weight based on the phenols of the general formula (1).

10. The method according to claim 2, wherein germanium oxide is added in the amount of from 0.1 to 30% by weight based on the phenols of the general formula (1).

* * * * *